United States Patent
Palti (10) Patent No.: US 9,750,431 B2
(45) Date of Patent: Sep. 5, 2017

(54) PULMONARY COMPLIANCE AND AIR FLOW RESISTANCE

(71) Applicant: Yoram Palti, Haifa (IL)

(72) Inventor: Yoram Palti, Haifa (IL)

(73) Assignee: Echosense Jersey Limited, St. Helier (JE)

( * ) Notice: Subject to any disclaimer, the term of this patent is extended or adjusted under 35 U.S.C. 154(b) by 587 days.

(21) Appl. No.: 14/467,558

(22) Filed: Aug. 25, 2014

(65) Prior Publication Data

US 2015/0057559 A1 Feb. 26, 2015

Related U.S. Application Data

(60) Provisional application No. 61/869,919, filed on Aug. 26, 2013.

(51) Int. Cl.
*A61B 5/08* (2006.01)
*A61B 5/085* (2006.01)
(Continued)

(52) U.S. Cl.
CPC .............. *A61B 5/085* (2013.01); *A61B 5/087* (2013.01); *A61B 5/091* (2013.01); *A61B 5/097* (2013.01); *A61B 5/7239* (2013.01); *A61B 5/7242* (2013.01)

(58) Field of Classification Search
CPC ....... A61B 5/087; A61B 5/085; A61B 5/7239; A61B 5/097; A61B 5/7242; A61B 5/091
See application file for complete search history.

(56) References Cited

U.S. PATENT DOCUMENTS 2,089,432 A * 8/1937 Ryan .................. G01L 7/00
55/DIG. 33
3,036,569 A * 5/1962 Clements ............... A61B 5/085
600/533
(Continued)

FOREIGN PATENT DOCUMENTS

DE 19734203 2/1999
WO 2013098714 7/2013

OTHER PUBLICATIONS

Cheng, et al., "Pulmonary resistance and state of inflation of lungs in normal subjects and in patients with airway obstruction," J Appl Physiol Sep. 1959; 14(5):727-732.*

(Continued)

*Primary Examiner* — Navin Natnithithadha
*Assistant Examiner* — Eric Messersmith
(74) *Attorney, Agent, or Firm* — Potomac Law Group, PLLC (57) ABSTRACT

Methods and apparatuses are described for direct rapid measurement of pulmonary flow resistance. A measurement of a first pressure in a gas-tight chamber is received from a pressure sensor when a gas output port of the chamber is closed, a patient is blowing into a gas inlet of the chamber at a given pressure, and a gas-flow path between the inlet and output port has a resistance value. A measurement of a second pressure in the chamber is received from the pressure sensor and a measurement of gas flow through the chamber is received from a gas flow sensor when the output port is opened and the patient is blowing into the inlet to maintain the given pressure relatively constant. A pulmonary flow resistance is computed based upon the measurement of the first pressure, the measurement of the second pressure, the resistance value, and the measurement of gas flow.

27 Claims, 6 Drawing Sheets

(51) Int. Cl.
  *A61B 5/087* (2006.01)
  *A61B 5/00* (2006.01)
  *A61B 5/091* (2006.01)
  *A61B 5/097* (2006.01)

(56) References Cited

U.S. PATENT DOCUMENTS

| | | | | |
|---|---|---|---|---|
| 4,031,885 | A | * | 6/1977 | Davis ............ A61B 5/085 600/533 |
| 4,036,222 | A | * | 7/1977 | Gillard ........... A61B 5/085 600/533 |
| 4,082,088 | A | * | 4/1978 | Franetzki ........ A61B 5/085 600/533 |
| 4,802,492 | A | * | 2/1989 | Grunstein ........ A61B 5/085 600/533 |
| 5,233,998 | A | * | 8/1993 | Chowienczyk ... A61B 5/0803 600/533 |
| 5,261,397 | A | * | 11/1993 | Grunstein ........ A61B 5/085 128/204.18 |
| 5,522,397 | A | * | 6/1996 | Vermaak ......... A61B 5/087 600/529 |
| 5,720,709 | A | * | 2/1998 | Schnall .......... A61B 5/085 128/204.21 |
| 5,868,681 | A | * | 2/1999 | Schiller ......... F16D 3/02 600/533 |
| 5,876,352 | A | * | 3/1999 | Weismann ....... A61B 5/085 600/529 |
| 6,066,101 | A | | 5/2000 | Johnson et al. |
| 6,355,003 | B1 | * | 3/2002 | Aviv ............ A61B 1/233 600/560 |
| 2004/0097821 | A1 | * | 5/2004 | Blomberg ........ A61B 5/085 600/529 |
| 2008/0234595 | A1 | * | 9/2008 | Ranieri .......... A61B 5/085 600/538 |
| 2013/0102917 | A1 | * | 4/2013 | Colbaugh ........ A61M 16/00 600/533 |

OTHER PUBLICATIONS

Mead, et al., "Evaluation of Airway Interruption Technique as a Method for Measuring Pulmonary Air-Flow Resistance," J Appl Physiol Jan. 1954; 6(7):408-416.*

Shaw, et al. "A new method for measurement of respiratory resistance," J Appl Physiol Feb. 1983; 54(2):594-597.*

Grunstein et al., "Expiratory volume clamping: a new method to assess respiratory mechanics in sedated infants," J Appl Physiol May 1987; 62(5) 2107-2114.*

Hall, et al., "Evaluation of the interrupter technique in healthy, unsedated infants," Eur Respir J 2001; 18: 982-988.*

Kochi, et al., "Chest wall and respiratory system mechanics in cats: effects of flow and volume." J Appl Physiol (1985). Jun. 1988;64(6):2636-46.*

Bridge, et al., "A portable device based on the interrupter technique to measure bronchodilator response in schoolchildren," Eur Respir J, 1996, 9, 1368-1373.*

Guidelines for the Diagnosis and Management of Asthma (NIH Publication No. 08-5846 ed.). National Institutes of Health. 2007, 74 pages.

Liistro, G., et al; Reassessment of the interruption technique for measuring flow resistance in humans. J Appl Physiol. Sep. 1989; 67(3); pp. 933-937.

Search Report and Written Opinion in corresponding PCT/IB2014/002571, dated Mar. 24, 2015, 15 pages.

* cited by examiner

For $Rr = \infty$ $Pa = P_T$      As Measured $Fp = Fr = 0$

— — — — — — — — — — —

For $Rr$ = Any other Value $$Fp = \frac{Pa - P_T}{Rp}$$

$$Fr = \frac{P_T - 0}{Rr}$$

As $Fp = Fr$ $$\frac{Pa - P_T}{Rp} = \frac{P_T}{Rr}$$

$$\frac{Pa}{Rp} - \frac{P_T}{Rp} = \frac{P_T}{Rr}$$

$$\frac{Pa}{Rp} = P_T \left(\frac{1}{Rp} + \frac{1}{Rr}\right)$$

$$Pa = P_T \left(\frac{Rp}{Rp} + \frac{Rp}{Rr}\right)$$

$$\boxed{Pa = P_T \left(1 + \frac{Rp}{Rr}\right)}$$

FIG. 4

PULMONARY COMPLIANCE AND AIR FLOW RESISTANCE

CROSS REFERENCE TO RELATED APPLICATIONS

This application claims the benefit of U.S. Provisional Patent Application No. 61/869,919, filed Aug. 26, 2013, which is incorporated herein by reference.

BACKGROUND

Living organisms require oxygen supply and removal of $CO_2$ to maintain their life and activity. In land based animals this is achieved by the respiratory system that pumps air into and out of the lungs and enables the required gas exchange between the inspired air and the circulating blood. In general terms the respiratory process is based on the passage of air through the mouth to the alveoli. Once air progresses through the mouth or nose, it travels through the oropharynx, nasopharynx, the larynx, the trachea, and a progressively subdividing system of bronchi and bronchioles of smaller and smaller diameter until it finally reaches the alveoli where the gas exchange of carbon dioxide and oxygen takes place.

The drawing and expulsion of air (ventilation or breathing) is driven by muscular action. Breathing is largely driven by the muscular diaphragm at the bottom of the thorax. Contraction of the diaphragm pulls the bottom of the cavity in which the lung is enclosed downward, increasing volume and thus decreasing pressure, causing air to flow into the airways. During normal breathing, expiration is passive and no muscles are contracted (the diaphragm relaxes). The rib cage itself is also able to expand and contract to some degree, through the action of other respiratory and accessory respiratory muscles. As a result, air is transported into or expelled out of the lungs. Air flow is dependent on the pressure gradient (between the alveoli and ambient air) and the resistance to flow in the described pathways (bronchi, bronchioles, etc.).

In a variety of diseases, for example COPD (chronic obstructive pulmonary disease) and specifically emphysema and asthma, the airways are narrowed such that the resistance to air flow (R) is increased resulting in flow limitation. Under such conditions and especially during exercise etc. the patient may suffer from lack of oxygen, increase of the level of blood $CO_2$ and the corresponding pH changes, etc. Note that in the US alone the number of patients suffering from the above is in excess of 20 million.

Pulmonary function tests (such as those described in Expert Panel Report 3: Guidelines for the Diagnosis and Management of Asthma (NIH Publication Number 08-5846 ed.). National Institutes of Health. 2007) are commonly used to diagnose and evaluate the state of air flow restrictive diseases. These tests include means for direct measurement of R. This measurement involves placement of the patient in a hermetically closed chamber while having him breathe through a pipe leading to the outside. This is an expensive and inconvenient test and only few specialized clinics carry it out. The alternative method "interrupted flow" proposed in Reassessment of the interruption technique for measuring flow resistance in humans. Liistro G, Stănescu D, Rodenstein D, Verner C.; Reassessment of the interruption technique for measuring flow resistance in humans. J Appl Physiol. 1989 September; 67(3):933-7 was proved inaccurate.

SUMMARY OF THE INVENTION

The invention, in one aspect, features a device for measuring pulmonary flow resistance. The device comprises a housing that defines a gas-tight chamber, the chamber having a gas inlet and a gas output port and a gas-flow path between the gas inlet and the gas output port, the gas-flow path having a first resistance value, wherein the gas output port is configured to switch selectively between (i) an open position in which gas can flow out of the chamber through the gas output port and (ii) a closed position in which gas flow out of the chamber is blocked. The device further comprises a gas flow sensor configured to measure flow of gas through the chamber and a pressure sensor configured to measure pressure in the chamber. The device further comprises a controller configured to (a) receive, when the output port is closed and a patient is blowing into the gas inlet at a given pressure, a measurement of a first pressure from the pressure sensor, (b) receive, after step (a) has been performed, and when the gas output port is opened and the patient is blowing into the gas inlet so as to maintain the given pressure relatively constant, a measurement of a second pressure from the pressure sensor and a measurement of a first gas flow from the gas flow sensor, and (c) compute a first pulmonary flow resistance based upon the measurement of the first pressure, the measurement of the second pressure, the first resistance value, and the measurement of the first gas flow.

The above aspect can include one or more of the following features. In some embodiments, the gas inlet comprises a mouthpiece. In some embodiments, the device further comprises an actuator configured to open and close the gas output port in response to a control signal received from the controller, and the controller is configured to send the control signal to open the gas output port after step (a) has been performed and before step (b) is performed. In some embodiments, the device further comprises a display configured to show at least one of: the measurement of the first pressure, the measurement of the second pressure, the measurement of the first gas flow, the first resistance value, and the first pulmonary flow resistance. In some embodiments, the device further comprises a display configured to indicate to the patient when to start and/or stop blowing into the gas inlet in response to a second control signal received from the controller, and the controller is configured to send the second control signal to the display before step (a) is performed.

In some embodiments, the first pulmonary flow resistance (Rp) is calculated using the following equation: $(Rp+Rr)=Pa/F$, wherein Rr is the first resistance value, Pa is estimated based upon the measurement of the second pressure, and F is the measurement of the first gas flow. In some embodiments, Pa is calculated by extrapolating the measurement of the second pressure versus time curve back to a time at which the gas output port is opened. In some embodiments, the controller is further configured to compute a pulmonary compliance (C) of the patient using the following equation: $C=\Delta V/\Delta P$, where $\Delta V$ is change in pulmonary volume and $\Delta P$ is change in pulmonary pressure. In some embodiments, the first resistance value is predetermined.

The invention, in another aspect, features a method for measuring pulmonary flow resistance. The method comprises the steps of (a) receiving, when a gas output port of a gas-tight chamber is closed and a patient is blowing into a gas inlet of the chamber at a given pressure, a measurement of a first pressure in the chamber from a pressure sensor, where a gas-flow path between the gas inlet and the gas output port has a first resistance value; (b) receiving, after step (a) has been performed, and when the gas output port is opened and the patient is blowing into the gas inlet so as to maintain the given pressure relatively constant, a measurement of a second pressure in the chamber from the pressure sensor and a measurement of a first gas flow through the chamber from a gas flow sensor; and (c) computing a first pulmonary flow resistance based upon the measurement of the first pressure, the measurement of the second pressure, the first resistance value, and the measurement of the first gas flow.

The above aspect can include one or more of the following features. In some embodiments, the first pulmonary flow resistance (Rp) is calculated using the following equation: (Rp+Rr)=Pa/F, wherein Rr is the first resistance value, Pa is estimated based upon the measurement of the second pressure, and F is the measurement of the first gas flow. In some embodiments, Pa is calculated by extrapolating the measurement of the second pressure versus time curve back to a time at which the gas output port is opened. In some embodiments, the method further comprises the step of computing a pulmonary compliance (C) of the patient using the following equation: $C=\Delta V/\Delta P$, wherein $\Delta V$ is change in pulmonary volume over time and $\Delta P$ is change in pulmonary pressure over time. In some embodiments, the first resistance value is predetermined.

In some embodiments, the method further comprises the steps of: (d) modifying the gas-flow path to have a second resistance value; (e) receiving, when the output port is closed and a patient is blowing into the gas inlet so as to maintain a second given pressure relatively constant, a measurement of a third pressure from the pressure sensor; (f) receiving, after steps (d) and (e) have been performed, and when the gas output port is opened and the patient is blowing into the gas inlet so as to maintain the second given pressure relatively constant, a measurement of a fourth pressure from the pressure sensor and a measurement of a second gas flow from the gas flow sensor; and (g) computing a second pulmonary flow resistance based upon the measurement of the third pressure, the measurement of the fourth pressure, the second resistance value, and the measurement of the second gas flow. In some embodiments, the method further comprises the step of: (h) generating a resistance-to-flow curve depicting pulmonary resistance versus pulmonary flow and a resistance-to-pressure curve depicting pulmonary resistance versus pulmonary pressure, by taking measurements at different blowing pressures and/or resistance values.

The invention, in another aspect, features a method for measuring pulmonary flow resistance. The method comprises the steps of: (a) closing a gas output port of a gas-tight chamber, the chamber having a gas inlet; (b) setting a gas flow resistor disposed in a gas-flow path between the inlet and the outlet port to a first resistance value; (c) receiving, after steps (a) and (b) have been performed and when a patient is blowing into the gas inlet at a given pressure, a measurement of a first pressure in the chamber from a pressure sensor; (d) opening, after step (c) has been performed, the gas output port; (e) receiving, after step (d) has been performed and when the patient is blowing into the gas inlet so as to maintain the given pressure relatively constant, a measurement of a second pressure in the chamber from the pressure sensor and a measurement of a first gas flow through the chamber from a gas flow sensor; and (f) computing a first pulmonary flow resistance based upon the measurement of the first pressure, the measurement of the second pressure, the first resistance value, and the measurement of the first gas flow.

The invention, in another aspect, features a device for measuring pulmonary flow resistance. The device comprises a housing that defines a gas-tight chamber, the chamber having a gas inlet and a gas output port and a gas-flow path between the gas inlet and the gas output port, wherein the gas output port is configured to switch selectively between (i) an open position in which gas can flow out of the chamber through the gas output port and (ii) a closed position in which gas flow out of the chamber is blocked. The device further comprises a gas flow sensor configured to measure flow of gas through the chamber, a pressure sensor configured to measure pressure in the chamber, and a gas flow resistor disposed in the gas-flow path, configured to be adjustable by a control input. The device further comprises a controller configured to (a) set the gas flow resistor to a first resistance value by sending a first control signal to the control input, (b) receive, when the output port is closed and a patient is blowing into the gas inlet at a given pressure, a measurement of a first pressure from the pressure sensor, (c) receive, after steps (a) and (b) have been performed, and when the gas output port is opened and the patient is blowing into the gas inlet so as to maintain the given pressure relatively constant, a measurement of a second pressure from the pressure sensor and a measurement of a first gas flow from the gas flow sensor, and (d) compute a first pulmonary flow resistance based upon the measurement of the first pressure, the measurement of the second pressure, the first resistance value, and the measurement of the first gas flow.

The above aspect can include one or more of the following features. In some embodiments, the gas inlet comprises a mouthpiece. In some embodiments, the device further comprises an actuator configured to open and close the gas output port in response to a second control signal received from the controller, and the controller is configured to send the second control signal to open the gas output port after step (a) has been performed and before step (b) is performed. In some embodiments, the device further comprises a display configured to show at least one of: the measurement of the first pressure, the measurement of the second pressure, the measurement of the first gas flow, the first resistance value, and the first pulmonary flow resistance. In some embodiments, the device further comprises a display configured to indicate to the patient when to start and/or stop blowing into the gas inlet in response to a third control signal received from the controller, and the controller is configured to send the third control signal to the display before step (a) is performed.

In some embodiments, the first pulmonary flow resistance (Rp) is calculated using the following equation: (Rp+Rr)=Pa/F, wherein Rr is the first resistance value, Pa is estimated based upon the measurement of the second pressure, and F is the measurement of the first gas flow. In some embodiments, Pa is calculated by extrapolating the measurement of the second pressure versus time curve back to a time at which the gas output port is opened. In some embodiments, the controller is further configured to compute a pulmonary compliance (C) of the patient using the following equation: $C=\Delta V/\Delta P$, wherein $\Delta V$ is change in pulmonary volume and $\Delta P$ is change in pulmonary pressure.

In some embodiments, the controller is further configured to (e) set the gas flow resistor to a second resistance value by sending a fourth control signal to the control input, (f) receive, when the output port is closed and a patient is blowing into the gas inlet so as to maintain a second given pressure relatively constant, a measurement of a third pressure from the pressure sensor, (g) receive, after steps (e) and (f) have been performed, and when the gas output port is opened and the patient is blowing into the gas inlet so as to maintain the second given pressure relatively constant, a measurement of a fourth pressure from the pressure sensor and a measurement of a second gas flow from the gas flow sensor, and (h) compute a second pulmonary flow resistance based upon the measurement of the third pressure, the measurement of the fourth pressure, the second resistance value, and the measurement of the second gas flow. In some embodiments, the controller is further configured to (i) generate a resistance-to-flow curve depicting pulmonary resistance versus pulmonary flow and a resistance-to-pressure curve depicting pulmonary resistance versus pulmonary pressure, by taking measurements at different blowing pressures and/or resistance values.

DESCRIPTION OF THE PREFERRED EMBODIMENTS

Figure 1A:
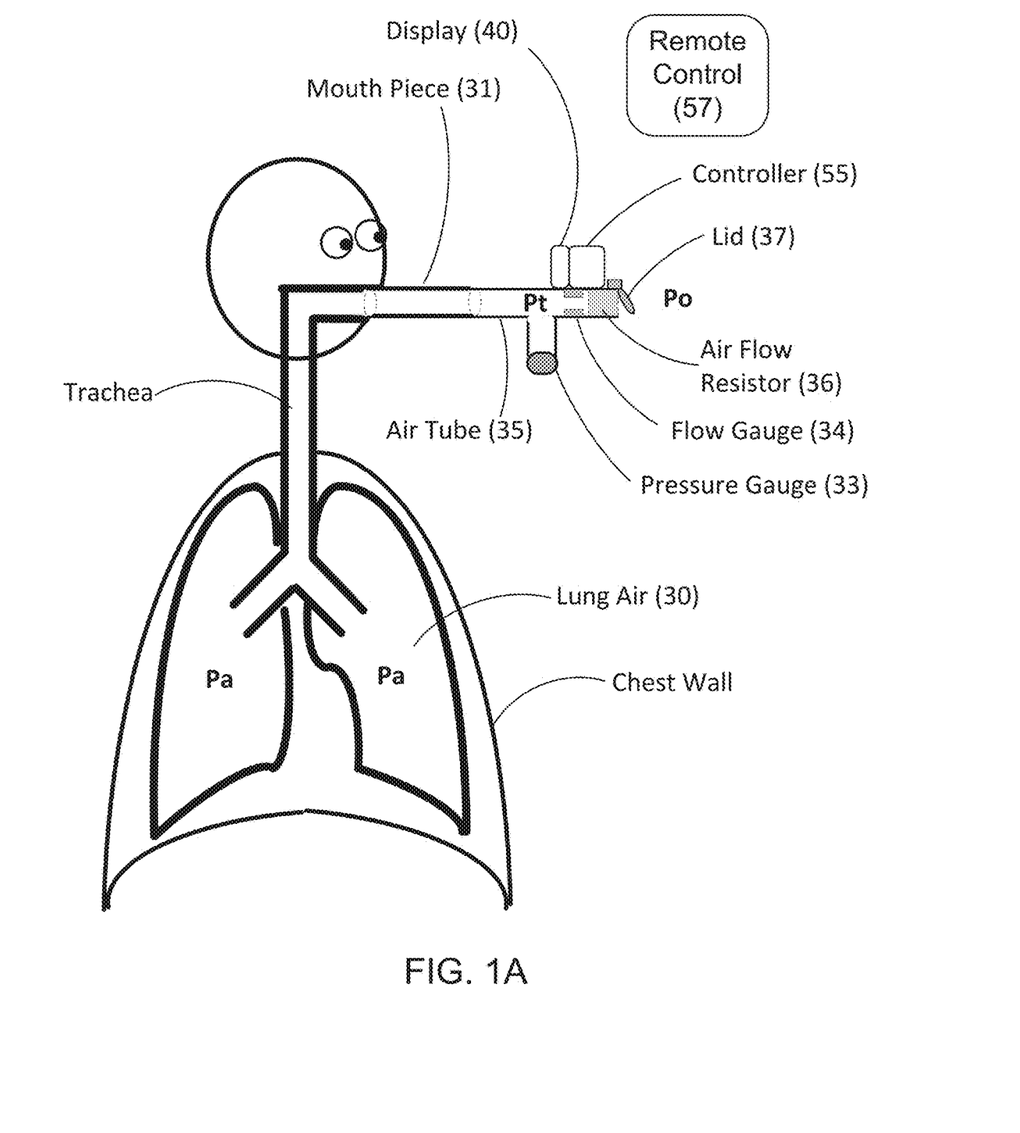
FIG. 1A is an exemplary schematic representation of a device for measuring pulmonary flow resistance.
Figure 1B:
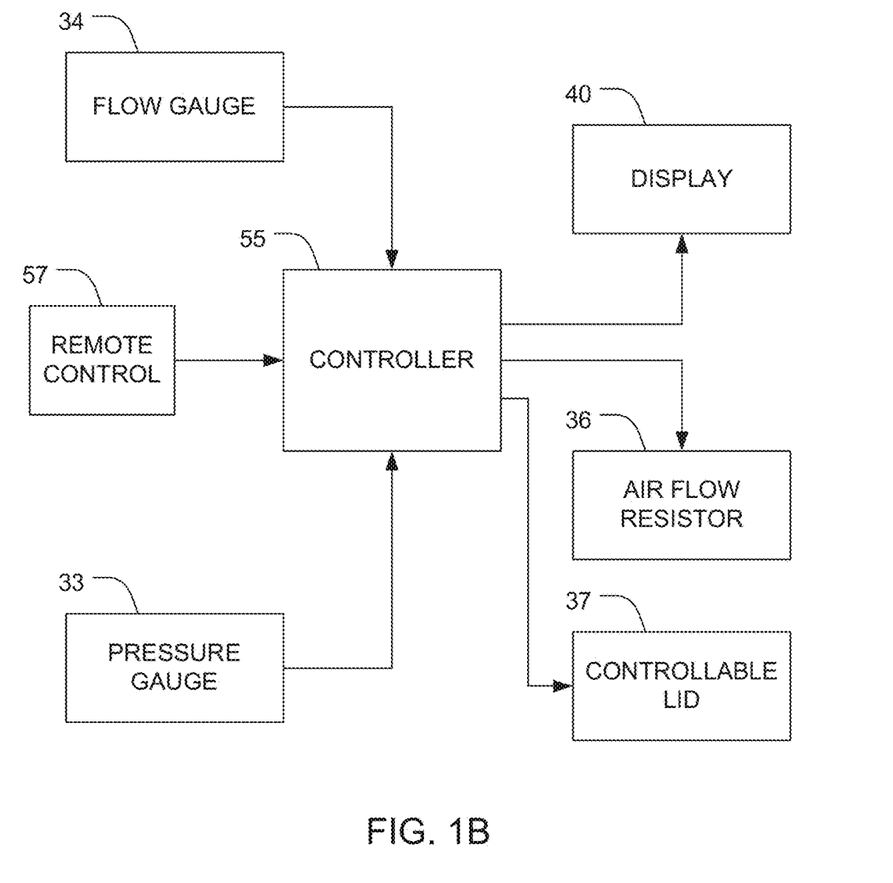
FIG. 1B is a functional block diagram of a device for measuring pulmonary flow resistance.

The Pulmonary Resistance Compliance Gauge (PRCG) is a simple device, which can be hand held, for direct rapid measurement of pulmonary airflow resistance and lung compliance. FIG. 1A is a schematic representation of an embodiment of the various components of the PRCG, and FIG. 1B is a functional block diagram of an embodiment of the PRCG.

The PRCG includes a housing that defines a gas-tight chamber. One example of a housing is air tube 35. The chamber has a gas inlet and a gas output port. A mouthpiece 35 can optionally be attached to the gas inlet. The gas output port is configured to switch selectively between (a) an open position in which gas can flow out of the chamber through the gas output port and (b) a closed position in which gas flow out of the chamber is blocked. An example gas output port is lid 37 depicted in FIG. 1A. In alternative embodiments the gas output port can also comprise, for example, a flap, shutter, or cap. The gas output port can optionally include an actuator configured to open and close the gas output port in response to a control signal received from the controller 55.

The PRCG also includes a pressure sensor configured to measure pressure in the chamber, and a gas flow sensor configured to measure flow of gas through the chamber. An example pressure sensor is pressure gauge 33 depicted in FIG. 1A, and an example gas flow sensor is flow gauge 34 in FIG. 1A.

The chamber also has a gas-flow path between the gas inlet and the gas outlet port, and this gas-flow path has a first resistance value. The resistance may be provided by a gas flow resistor. An example gas flow resistor is air flow resistor 36 depicted in FIG. 1A. In a preferred embodiment, the gas flow resistor is configured to be adjustable by a control input. The control input receives a control signal from the controller 55 and adjusts a resistance of the gas flow resistor according to the control signal.

The gas flow resistor can take a variety of forms. For example, the resistor can be a tube made with walls of a malleable material (e.g., rubber) that has a gas-tight seal on each end to the chamber. The walls of the tube can be pinched or compressed to narrow its inner channel and provide increased resistance to gas flow.

In another example, a rotating wheel comprising a plurality of tubes each having a different inner channel diameter can be coupled to the device. As the wheel rotates, a different tube can be moved into the gas-flow path and form a gas-tight seal with the device, thereby providing a different resistance to gas flow. In some embodiments, the wheel is coupled to a motor that operates to rotate the wheel between different tubes and the controller can provide a control signal to the motor for rotation of the wheel.

In alternative embodiments, the resistance setting of the gas flow resistor is configured to be adjusted manually. For example, tubes having varying inner channel diameters can be swapped into the gas-flow path by the user in order to adjust the gas flow resistance.

The measurement performed by the PRCG relies in part on the principle that when there is no air flow in a system of interconnected compartments there are no pressure differences. Thus, if one measures the air pressure at one location (e.g., by measuring the pressure $P_T$ in the tube 35), the measured value represents correctly the pressure in all the system compartments (including, the pressure Pa in the lung air 30).

The PRCG also includes a controller 55 (e.g., a processor) that is programmed to accept measurements from the pressure sensor and the gas flow sensor, and perform the computations of pulmonary resistance and pulmonary compliance as described herein. In embodiments where the gas output port is automatically controlled, the controller 55 sends controls signals to a control input coupled to the gas output port to open and close the output port. Alternatively, in embodiments where the gas output port is manually controlled, the gas output port is opened and closed by, e.g., a user of the device manipulating the gas output port to switch the port between open and closed positions. The device can optionally provide instructions to the user regarding the manual operation of the gas output port.

In embodiments where the resistance value of the gas flow resistor is automatically controlled, the controller 55 sends control signals to the gas flow resistor to control the resistance to a desired value. Alternatively, in embodiments where the resistance value of the gas flow resistor is manually controlled, the gas flow resistor can be swapped out of the gas-flow path for another resistor having a different inner channel diameter or the gas flow resistor can be adjusted (e.g., by pinching or compressing a tube) to change its resistance value.

Optionally, the controller 55 is programmed to send control signals to the display 40 for presentation of measurements and/or activation of indicators (e.g., LEDs) on the display.

Figure 2A:
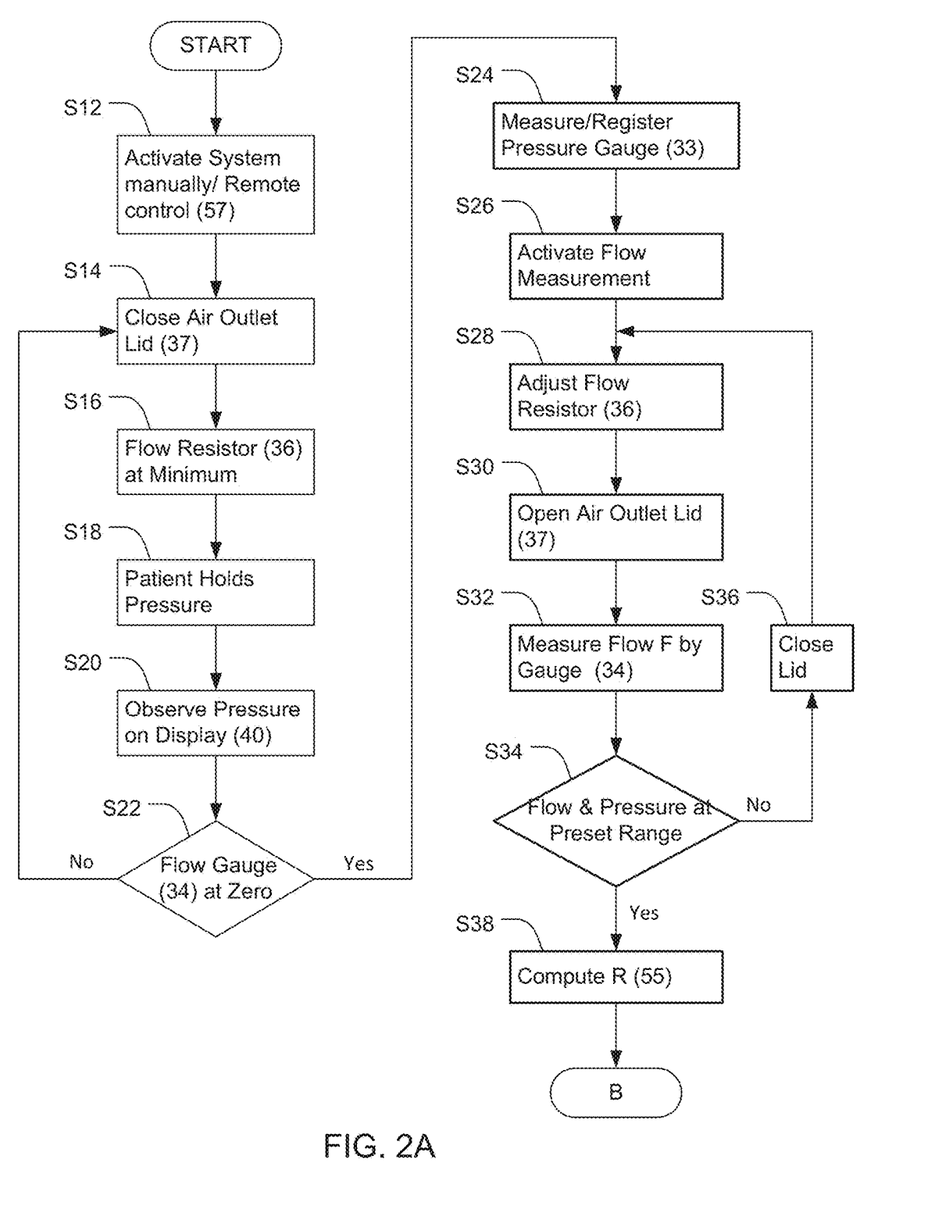
FIG. 2A is a flow diagram of a method for measuring pulmonary flow resistance.

Referring to FIG. 2A, the PRCG can be activated manually or by means of remote control 57 in step S12.

An initial pressure measurement of Pa is made indirectly by measuring $P_T$ when there is no air flow, F. This initial measurement of Pa may be obtained, for example, when the patient tries to inspire or expire (including forced expiration) into the mouth-piece 31 that leads to the air tube 35, the outlet port of which is closed (e.g., by lid 37).

This may be accomplished, e.g., by closing the lid 37 in step S14 and instructing the patient to blow into the mouthpiece 31 of the tube 35 at a given pressure. At this time the air flow resistor 36 is optionally set to its minimal resistance value in step S16. Under these conditions the pressure gauge 33 (which measures $P_T$) measures the pressure in the whole system (including the alveolar air pressure Pa). This pressure (i.e., the first pressure measurement) is reported to the controller 55, and the controller 55 sends the pressure reading to the display 40. The patient is asked to hold the given pressure relatively constant for a short while (e.g., between 1 and 4 seconds) in step S18 by doing a Valsalva maneuver and to observe the pressure on display 40 in step S20. An example of a suitable pressure for this step is 10 mm Hg. Optionally, an LED (not shown) may be illuminated on or near the display 40 to inform the patient when to start and stop maintaining the given pressure. If it is determined in step S22 that the flow as recorded by the flow gauge 34 is zero, the pressure $P_T$ that is measured by the pressure gauge 33 is registered in step S24 by the controller 55 as being Pa under zero-flow conditions. On the other hand, if non-zero flow is detected in step S22, then the lid 37 may not be closed properly, so the process returns to step S14 to try again.

Figure 4:
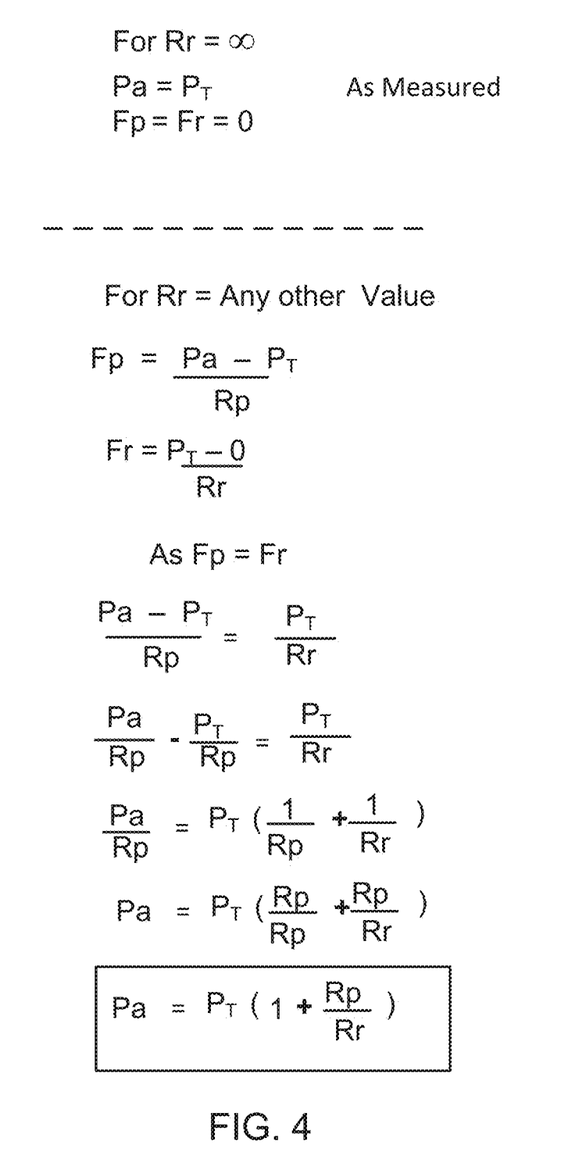
FIG. 4 is an exemplary set of equations to determine pulmonary pressure.

In step S26 the controller 55 activates the flow gauge 34 so that the controller 55 can monitor the flow in the tube 35. In embodiments that include automatic setting of the air flow resistor, the controller 55 sends a command to the air flow resistor 36 and sets the resistor 36 to a selected relatively large resistance value, Rr, in step S28. The lid 37 is then opened in step S30 in response to a command from the controller 55. (In alternative embodiments the lid 37 is opened manually). The value of Rr can be one of a series of known values, and is preferably in the range of the pulmonary air resistance. Alternatively Rr can be determined dynamically as described below. When the resistance is not infinite, there will be some flow, and FIG. 4 provides a set of equations that can be used to compute Pa.

Figure 3:
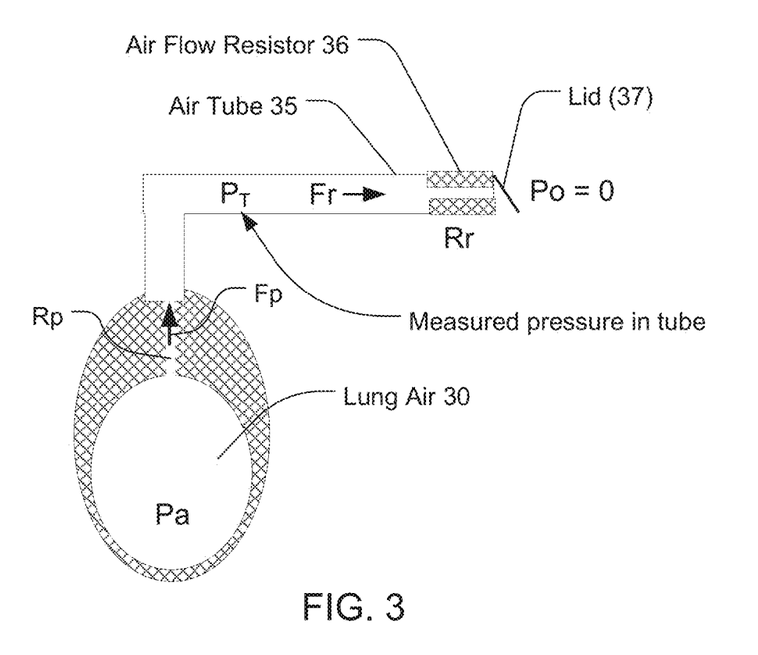
FIG. 3 is a diagram depicting the flows and pressures in various parts of the system.

FIG. 3 depicts the flows and pressures that exist at various points in the system. In FIG. 3, Pa is the pressure in the lungs, $P_T$ is the pressure in the tube (which can be measured by the pressure gauge 33 shown in FIG. 1), and $P_0$ is the pressure in the outside air. Rp is the pulmonary air flow resistance and Rr is the resistance of the air flow resistor 36 (shown in FIG. 1A). Fp is the pulmonary air flow and Fr is the flow through the air flow resistor (which can be measured by the flow gauge 34 shown in FIG. 1A). Note that when the seal is tight between the patient's mouth and the mouth-piece 31, and when no air is leaking out of the patient's nose (both of which should be verified when the system is being used), Fp will be equal to Fr.

The patient is instructed to maintain the given pressure (e.g., that he sees on display 40) relatively constant for an additional period of time (e.g., 1 to 5 seconds) following the moment that the lid 37 is opened (i.e., $t_0$). Again, after it is determined that the pressure $P_T$ as recorded by pressure gauge 33 is stable, while flow, F, is measured by flow gauge 34 in step S32. Both flow F (i.e., the first flow measurement) and pressure $P_T$ (i.e., the second pressure measurement) are reported from the respective gauges to the controller 55 and registered by the controller 55. During this step, the flow F is preferably low (e.g., in the range of 5-50 cm$^3$/s) such that the volume leak out of the lung is sufficiently small so that the alveolar pressure change is under 5%. As the total lung volume is in the order of 4-6 liters, a leak of 10 cm$^3$ lasting 5 sec will cause a volume and pressure change of about 1%. Note that the flow gauge 34 should preferably be highly sensitive in the low-flow range.

The readings obtained during this portion of the procedure depend on the patient maintaining the given pressure relatively constant. A test is done in step S34 to see if this was done properly. If it was, processing continues in step S38, where R is computed by the controller 55. If the pressure was not maintained properly, processing continues in step S36 where the lid 37 is closed, and then returns to step S28 to make another attempt.

Pa can be estimated based on the measured $P_T$ by assuming that the Pa change is negligible immediately after opening the lid. Alternatively Pa can be computed from $P_T$ by extrapolating the $P_T$ vs. time curve back to the lid opening time, $t_0$.

The air flow, F, as measured by flow gauge 34 is determined by the driving force (Pa−Po), where Po is the ambient pressure. However as Po=0, the driving force is Pa alone. The second factor that affects F is the total resistance to air flow, R. R is the sum of two resistors in series: the pulmonary air flow resistance, Rp, and the air flow resistor 36, Rr. Since R=Pa/F, R can be computed, in step S38, based on the measured F and the estimated Pa. In addition, $$R=(Rp+Rr)=Pa/F. \quad \text{Equation 1}$$

So for a known Rr, the pulmonary resistance Rp can be calculated using eq. 1.

Rr can also be measured dynamically as follows: Set Rr to the level to be used. Open the lid 37 and apply the desired pressure (so as to generate flow of the desired level at which Rr is to be determined) to the mouth piece 31. Measure the flow, Fr, through the flow gauge 34 under these conditions. As the pressure gauge 33 measures $P_T$ at one end of Rr and as on its other side Po=0, $P_T$ is the pressure gradient across Rr and thus:

$$Rr=Pa/Fr \quad \text{Equation 2}$$

The measurement of Rp can be repeated at various initial Pa values, by asking the patient to maintain different pressures and repeating steps S12 through S38 (or, alternatively, repeating only steps S24-S34), and on this basis R vs. P curves can be constructed. Similarly, R measurement can be repeated at various flow values, by asking the patient to maintain different pressures and or adjusting air flow resistor 36 to different values and repeating steps S26 through S38, and on this basis R vs. Flow and R vs. P curves can be constructed. For example, the resistance of the gas-flow path can be set to a second resistance value, then when the output port is closed and while a patient is blowing into the gas inlet so as to maintain a second given pressure relatively constant, a measurement of a third pressure from the pressure sensor is received by the controller 55. Next, the gas output port is opened while the patient is blowing into the gas inlet so as to maintain the second given pressure relatively constant, and the controller 55 receives a measurement of a fourth pressure from the pressure sensor and a measurement of a second gas flow from the gas flow sensor. The controller 55 then computes a second pulmonary flow resistance based upon the measurement of the third pressure, the measurement of the fourth pressure, the second resistance value, and the measurement of the second gas flow. The patient may be allowed to rest between measurements.

Note that to obtain the desired low flows, Rr should preferably be controlled to have relatively high values. In addition, to determine Pa accurately, $P_T$ must be measured with high accuracy.

Figure 2B:
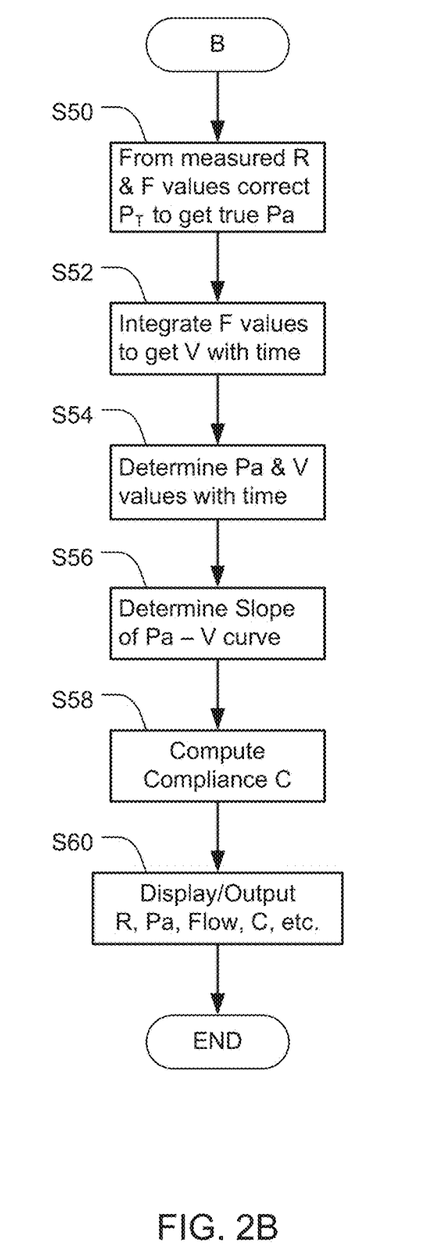
FIG. 2B is a flow diagram of a method for computing pulmonary compliance.

FIG. 2B shows a procedure implemented by the controller 55 for using the data obtained above to determine the lung compliance. It uses the flow values obtained in step S32 and the resistance value obtained in step S38 (as described above in connection with FIG. 2A). This procedure is preferably implemented while the air flow resistor 36 is set to a relatively low value so that the leak is significant such that Pa changes with time. As flow is not negligible, the measured $P_T$ now does not equal Pa. However, as the resistance to flow and the flow are known, the pressure drop can be calculated and $P_T$ corrected in step S50 so as to represent the true value of Pa.

In step S52, by integrating the leak flow so as to get the leak volume values with time, one gets the change in lung volumes, V. And in step S54, the corresponding changes in Pa are obtained. The slope of the P–V curve is then determined in step S56, and this is used to compute the compliance C in step S58. Compliance is defined as:

$$C=\Delta V/\Delta P \qquad \text{Equation 3}$$

Where $\Delta V$ is the change in volume and $\Delta P$ is the change in pressure. This relationship is usually constant over the physiological pressure range. Thus values obtained at different pressures can be averaged. In some embodiments, the controller 55 outputs the determined values for R, Pa, F, and C in step S60, e.g., to display 40.

The above C determination can be repeated for different lung inflations, etc. Note that the value of the resistance of the air flow resistor 36 can be determined as the flow and the pressure drop across it (as the external pressure, Po=0, the potential drop equals $P_T$) are measured in the system.

Conventional interfaces (not shown) are preferably used interfacing the various components depicted in FIG. 1B, and all the components are controlled by the controller 55 and/or send data to the controller 55. For example, a bluetooth interface may be used to interface the remote control 57 with the controller 55. Conventional digital interfaces may be used to send the readings from the flow gauge 34 and the pressure gauge 33 to the controller 55. The display 40 may be implemented using any conventional technology (e.g., LCD), and interfaced to the controller 55 in conventional ways. And, in embodiments where the air flow resistor 36 is automatically controlled, the air flow resistor 36 is configured to adjust its resistance value in response to a control signal issued by the controller 55 using any conventional approach (e.g., by having the controller 55 write the control signal to a particular address) to cause the activation of an actuator (e.g., a stepper motor). Similarly, in embodiments where the gas output port 37 is automatically controlled, the port may be opened and closed in response to a control signal issued by the controller 55 using any conventional approach (e.g., by having the controller 55 write the control signal to a particular address) to cause the activation of an actuator (e.g., a solenoid).

Finally, while the present invention has been disclosed with reference to certain embodiments, numerous modifications, alterations, and changes to the described embodiments are possible without departing from the sphere and scope of the present invention.

What is claimed is:

1. A device for measuring pulmonary flow resistance, the device comprising:
    a housing that defines a gas-tight chamber, the chamber having a gas inlet and a gas output port and a gas-flow path between the gas inlet and the gas output port, the gas-flow path having a first resistance value, wherein the gas output port is configured to switch selectively between (i) an open position in which gas can flow out of the chamber through the gas output port and (ii) a closed position in which gas flow out of the chamber is blocked;
    a gas flow sensor configured to measure flow of gas through the chamber;
    a pressure sensor configured to measure pressure in the chamber; and
    a controller configured to
        (a) receive, when the output port is closed and a patient is blowing into the gas inlet at a given pressure, a measurement of a first pressure from the pressure sensor,
        (b) determine, after step (a) has been performed and when the gas output port is opened, that the patient is blowing into the gas inlet so as to maintain the given pressure relatively constant,
        (c) receive a measurement of a second pressure from the pressure sensor and a measurement of a first gas flow from the gas flow sensor while the patient is blowing into the gas inlet so as to maintain the given pressure relatively constant, and
        (d) compute a first pulmonary flow resistance based upon the measurement of the first pressure, the measurement of the second pressure, the first resistance value, and the measurement of the first gas flow.

2. The device of claim 1, wherein the gas inlet comprises a mouthpiece.

3. The device of claim 1, further comprising an actuator configured to open and close the gas output port in response to a control signal received from the controller, and wherein the controller is configured to send the control signal to open the gas output port after step (a) has been performed and before step (b) is performed.

4. The device of claim 1, further comprising a display configured to show at least one of: the measurement of the first pressure, the measurement of the second pressure, the measurement of the first gas flow, the first resistance value, and the first pulmonary flow resistance.

5. The device of claim 1, further comprising a display configured to indicate to the patient when to start and/or stop blowing into the gas inlet in response to a second control signal received from the controller, and wherein the controller is configured to send the second signal to the display before step (a) is performed.

6. The device of claim 1, wherein the first pulmonary flow resistance (Rp) is calculated using the following equation: (Rp+Rr)=Pa/F, wherein Rr is the first resistance value, Pa is estimated based upon the measurement of the second pressure, and F is the measurement of the first gas flow.

7. The device of claim 6, wherein Pa is calculated by extrapolating the measurement of the second pressure versus time curve back to a time at which the gas output port is opened.

8. The device of claim 1, wherein the controller is further configured to compute a pulmonary compliance (C) of the patient using the following equation: $C=\Delta V/\Delta P$, wherein $\Delta V$ is change in pulmonary volume and $\Delta P$ is change in pulmonary pressure.

9. The device of claim 1, wherein the first resistance value is predetermined.

10. A method for measuring pulmonary flow resistance, the method comprising the steps of:
    (a) receiving, when a gas output port of a gas-tight chamber is closed and a patient is blowing into a gas inlet of the chamber at a given pressure, a measurement of a first pressure in the chamber from a pressure sensor, wherein a gas-flow path between the gas inlet and the gas output port has a first resistance value;

(b) receiving, after step (a) has been performed, and when the gas output port is opened and the patient is blowing into the gas inlet so as to maintain the given pressure relatively constant, a measurement of a second pressure in the chamber from the pressure sensor and a measurement of a first gas flow through the chamber from a gas flow sensor; and (c) computing a first pulmonary flow resistance based upon the measurement of the first pressure, the measurement of the second pressure, the first resistance value, and the measurement of the first gas flow.

11. The method of claim 10, wherein the first pulmonary flow resistance (Rp) is calculated using the following equation: (Rp+Rr)=Pa/F, wherein Rr is the first resistance value, Pa is estimated based upon the measurement of the second pressure, and F is the measurement of the first gas flow.

12. The method of claim 11, wherein Pa is calculated by extrapolating the measurement of the second pressure versus time curve back to a time at which the gas output port is opened.

13. The method of claim 10, further comprising the step of computing a pulmonary compliance (C) of the patient using the following equation: C=ΔV/ΔP, wherein ΔV is change in pulmonary volume over time and ΔP is change in pulmonary pressure over time.

14. The method of claim 10, wherein the first resistance value is predetermined.

15. The method of claim 10, further comprising the steps of:

(d) modifying the gas-flow path to have a second resistance value;

(e) receiving, when the output port is closed and a patient is blowing into the gas inlet so as to maintain a second given pressure relatively constant, a measurement of a third pressure from the pressure sensor;

(f) receiving, after steps (d) and (e) have been performed, and when the gas output port is opened and the patient is blowing into the gas inlet so as to maintain the second given pressure relatively constant, a measurement of a fourth pressure from the pressure sensor and a measurement of a second gas flow from the gas flow sensor; and (g) computing a second pulmonary flow resistance based upon the measurement of the third pressure, the measurement of the fourth pressure, the second resistance value, and the measurement of the second gas flow.

16. The method of claim 15, further comprising the step of (h) generating a resistance-to-flow curve depicting pulmonary resistance versus pulmonary flow and a resistance-to-pressure curve depicting pulmonary resistance versus pulmonary pressure, by taking measurements at different blowing pressures and/or resistance values.

17. A method for measuring pulmonary flow resistance, the method comprising the steps of:

(a) closing a gas output port of a gas-tight chamber, the chamber having a gas inlet;

(b) setting a gas flow resistor disposed in a gas-flow path between the inlet and the outlet port to a first resistance value;

(c) receiving, after step (a) and step (b) have been performed and when a patient is blowing into the gas inlet at a given pressure, a measurement of a first pressure in the chamber from a pressure sensor;

(d) opening, after step (c) has been performed, the gas output port;

(e) receiving, after step (d) has been performed and when the patient is blowing into the gas inlet so as to maintain the given pressure relatively constant, a measurement of a second pressure in the chamber from the pressure sensor and a measurement of a first gas flow through the chamber from a gas flow sensor; and (f) computing a first pulmonary flow resistance based upon the measurement of the first pressure, the measurement of the second pressure, the first resistance value, and the measurement of the first gas flow.

18. A device for measuring pulmonary flow resistance, the device comprising:

a housing that defines a gas-tight chamber, the chamber having a gas inlet and a gas output port and a gas-flow path between the gas inlet and the gas output port, wherein the gas output port is configured to switch selectively between (i) an open position in which gas can flow out of the chamber through the gas output port and (ii) a closed position in which gas flow out of the chamber is blocked;

a gas flow sensor configured to measure flow of gas through the chamber;

a pressure sensor configured to measure pressure in the chamber;

a gas flow resistor disposed in the gas-flow path, configured to be adjustable by a control input; and a controller configured to (a) set the gas flow resistor to a first resistance value by sending a first control signal to the control input, (b) receive, when the output port is closed and a patient is blowing into the gas inlet at a given pressure, a measurement of a first pressure from the pressure sensor, (c) determine, after steps (a) and (b) have been performed and when the gas output port is opened, that the patient is blowing into the gas inlet so as to maintain the given pressure relatively constant, (d) receive a measurement of a second pressure from the pressure sensor and a measurement of a first gas flow from the gas flow sensor while the patient is blowing into the gas inlet so as to maintain the given pressure relatively constant, and (e) compute a first pulmonary flow resistance based upon the measurement of the first pressure, the measurement of the second pressure, the first resistance value, and the measurement of the first gas flow.

19. The device of claim 18, wherein the gas inlet comprises a mouthpiece.

20. The device of claim 18, further comprising an actuator configured to open and close the gas output port in response to a second control signal received from the controller, and wherein the controller is configured to send the second control signal to open the gas output port after step (a) has been performed and before step (b) is performed.

21. The device of claim 18, further comprising a display configured to show at least one of: the measurement of the first pressure, the measurement of the second pressure, the measurement of the first gas flow, the first resistance value, and the first pulmonary flow resistance.

22. The device of claim 18, further comprising a display configured to indicate to the patient when to start and/or stop blowing into the gas inlet in response to a third control signal received from the controller, and wherein the controller is configured to send the third control signal to the display before step (a) is performed.

23. The device of claim 18, wherein the first pulmonary flow resistance (Rp) is calculated using the following equation: (Rp+Rr)=Pa/F, wherein Rr is the first resistance value, Pa is estimated based upon the measurement of the second pressure, and F is the measurement of the first gas flow.

24. The device of claim 23, wherein Pa is calculated by extrapolating the measurement of the second pressure versus time curve back to a time at which the gas output port is opened.

25. The device of claim 18, wherein the controller is further configured to compute a pulmonary compliance (C) of the patient using the following equation: $C=\Delta V/\Delta P$, wherein $\Delta V$ is change in pulmonary volume and $\Delta P$ is change in pulmonary pressure.

26. The device of claim 18, wherein the controller is further configured to
 (f) set the gas flow resistor to a second resistance value by sending a fourth control signal to the control input,
 (g) receive, when the output port is closed and a patient is blowing into the gas inlet so as to maintain a second given pressure relatively constant, a measurement of a third pressure from the pressure sensor,
 (h) receive, after steps (f) and (g) have been performed, and when the gas output port is opened and the patient is blowing into the gas inlet so as to maintain the second given pressure relatively constant, a measurement of a fourth pressure from the pressure sensor and a measurement of a second gas flow from the gas flow sensor, and
 (i) compute a second pulmonary flow resistance based upon the measurement of the third pressure, the measurement of the fourth pressure, the second resistance value, and the measurement of the second gas flow.

27. The device of claim 26, wherein the controller is further configured to
 (j) generate a resistance-to-flow curve depicting pulmonary resistance versus pulmonary flow and a resistance-to-pressure curve depicting pulmonary resistance versus pulmonary pressure, by taking measurements at different blowing pressures and/or resistance values.

* * * * *